United States Patent
Hewitt et al.

(10) Patent No.: US 12,180,511 B2
(45) Date of Patent: Dec. 31, 2024

(54) AUTOMATED PRODUCTION OF VIRAL VECTORS

(71) Applicant: LONZA WALKERSVILLE, INC., Walkersville, MD (US)

(72) Inventors: Matthew Hewitt, Walkersville, MD (US); Young Shin, Walkersville, MD (US); Bingnan Gu, Manvel, TX (US); Caitlin M. Guenther, Houston, TX (US); Anandita Seth, Sugar Land, TX (US)

(73) Assignee: LONZA WALKERSVILLE, INC, Walkersville, MD (US)

( * ) Notice: Subject to any disclaimer, the term of this patent is extended or adjusted under 35 U.S.C. 154(b) by 0 days.

(21) Appl. No.: 18/337,734

(22) Filed: Jun. 20, 2023

(65) Prior Publication Data

US 2024/0026306 A1    Jan. 25, 2024

Related U.S. Application Data (63) Continuation of application No. 16/720,227, filed on Dec. 19, 2019, now Pat. No. 11,718,833.

(60) Provisional application No. 62/949,848, filed on Dec. 18, 2019, provisional application No. 62/890,904, filed on Aug. 23, 2019, provisional application No. 62/866,092, filed on Jun. 25, 2019, provisional application No. 62/783,589, filed on Dec. 21, 2018.

(51) Int. Cl.
| | |
|---|---|
| *C12N 15/86* | (2006.01) |
| *A61K 9/00* | (2006.01) |
| *A61K 35/76* | (2015.01) |
| *C12N 5/10* | (2006.01) |
| *C12N 7/00* | (2006.01) |
| *C12N 7/01* | (2006.01) |
| *C12N 15/113* | (2010.01) |
| *C12N 15/861* | (2006.01) |
| *C12N 15/90* | (2006.01) |

(52) U.S. Cl.
CPC .............. *C12N 7/00* (2013.01); *A61K 9/0019* (2013.01); *A61K 9/007* (2013.01); *A61K 35/76* (2013.01); *C12N 15/86* (2013.01); *C12N 15/90* (2013.01); *C12N 2740/15043* (2013.01); *C12N 2740/15051* (2013.01); *C12N 2750/14143* (2013.01); *C12N 2750/14151* (2013.01)

(58) Field of Classification Search
CPC .......... C12N 15/86; C12N 2750/14152; C12N 2750/14143; C12N 2830/006; C12N 15/8645
See application file for complete search history.

(56) References Cited

U.S. PATENT DOCUMENTS

| | | |
|---|---|---|
| 4,642,120 A | 2/1987 | Nevo et al. |
| 4,939,151 A | 7/1990 | Bacehowski et al. |
| 5,041,138 A | 8/1991 | Vacanti et al. |
| 5,081,036 A | 1/1992 | Familletti |
| 5,240,854 A | 8/1993 | Berry et al. |
| 5,246,699 A | 9/1993 | Debre et al. |
| 5,424,209 A | 6/1995 | Kearney |
| 5,478,479 A | 12/1995 | Herrig |
| 5,549,134 A | 8/1996 | Browne et al. |
| 5,688,687 A | 11/1997 | Palsson et al. |
| 5,728,581 A | 3/1998 | Schwartz et al. |
| 5,786,207 A | 7/1998 | Katz et al. |
| 5,792,603 A | 8/1998 | Dunkelman et al. |
| 5,827,729 A | 10/1998 | Naughton et al. |
| 5,842,477 A | 12/1998 | Naughton et al. |
| 5,846,828 A | 12/1998 | Peterson et al. |
| 5,882,929 A | 3/1999 | Fofonoff et al. |
| 5,891,455 A | 4/1999 | Sittinger et al. |
| 5,902,741 A | 5/1999 | Purchio et al. |
| 5,906,934 A | 5/1999 | Grande et al. |
| 5,922,604 A | 7/1999 | Stapleton et al. |
| 5,928,936 A | 7/1999 | Ingram |
| 5,985,653 A | 11/1999 | Armstong et al. |
| 5,989,913 A | 11/1999 | Anderson et al. |
| 5,994,129 A | 11/1999 | Armstrong et al. |
| 6,048,721 A | 4/2000 | Armstrong et al. |
| 6,048,722 A | 4/2000 | Farb et al. |
| 6,060,306 A | 5/2000 | Flatt et al. |
| 6,096,532 A | 8/2000 | Armstrong et al. |
| 6,121,042 A | 9/2000 | Peterson et al. |
| 6,123,655 A | 9/2000 | Fell |
| 6,197,575 B1 | 3/2001 | Griffith et al. |
| 6,214,574 B1 | 4/2001 | Kopf |

(Continued)

FOREIGN PATENT DOCUMENTS

| | | |
|---|---|---|
| AU | 2002/324169 A1 | 3/2003 |
| DE | 4021123 A1 | 4/1991 |

(Continued)

OTHER PUBLICATIONS

Konstantin B. Konstantinov "Monitoring and Control of the Physiological State of Cell Cultures" Biotechnology and Bioengineering, vol. 52, pp. 271-289 (1996) (Year: 1996).

(Continued)

*Primary Examiner* — Barry A Chestnut (74) *Attorney, Agent, or Firm* — MEDLER FERRO WOODHOUSE & MILLS PLLC (57) ABSTRACT

The present disclosure provides an automated method of producing viral vectors, utilizing engineered viral vector-producing cell lines within a fully-enclosed cell engineering system. Exemplary viral vectors that can be produced include lentivirus vectors, adeno-associated virus vectors, baculovirus vectors and retrovirus vectors.

17 Claims, 3 Drawing Sheets

(56) References Cited

U.S. PATENT DOCUMENTS

| | | |
|---|---|---|
| 6,228,635 B1 | 5/2001 | Armstrong et al. |
| 6,238,908 B1 | 5/2001 | Armstrong et al. |
| 6,297,046 B1 | 10/2001 | Smith et al. |
| 6,323,146 B1 | 11/2001 | Pugh et al. |
| 6,402,941 B1 | 6/2002 | Lucido et al. |
| 7,348,175 B2 | 5/2008 | Vilendrer et al. |
| 7,906,323 B2 | 3/2011 | Cannon et al. |
| 8,492,140 B2 | 7/2013 | Smith et al. |
| 8,727,132 B2 | 5/2014 | Miltenyi et al. |
| 9,499,780 B2 | 11/2016 | Smith et al. |
| 9,534,195 B2 | 1/2017 | Smith et al. |
| 9,629,877 B2 | 4/2017 | Cooper et al. |
| 9,701,932 B2 | 7/2017 | Smith et al. |
| 9,783,768 B2 | 10/2017 | Larcher et al. |
| 10,253,316 B2 | 4/2019 | Masquelier et al. |
| 10,273,300 B2 | 4/2019 | Bedoya et al. |
| 11,208,626 B2 | 12/2021 | Mason et al. |
| 2001/0021529 A1 | 9/2001 | Takagi |
| 2001/0043918 A1 | 11/2001 | Masini et al. |
| 2002/0009797 A1 | 1/2002 | Wolf et al. |
| 2002/0009803 A1 | 1/2002 | Vajta |
| 2002/0025547 A1 | 2/2002 | Rao |
| 2002/0037580 A1 | 3/2002 | Schoeb |
| 2002/0146816 A1 | 10/2002 | Vellinger et al. |
| 2002/0155487 A1 | 10/2002 | Greenberger et al. |
| 2002/0179525 A1 | 12/2002 | Shaffer et al. |
| 2003/0032071 A1 | 2/2003 | Wang et al. |
| 2003/0040104 A1 | 2/2003 | Barbera-Guillem |
| 2003/0054335 A1 | 3/2003 | Taya et al. |
| 2003/0159946 A1 | 8/2003 | Eden et al. |
| 2003/0215935 A1 | 11/2003 | Coon |
| 2004/0048364 A1 | 3/2004 | Trosch |
| 2005/0064465 A1 | 3/2005 | Dettloff et al. |
| 2005/0130297 A1 | 6/2005 | Sarem et al. |
| 2005/0186671 A1 | 8/2005 | Cannon et al. |
| 2015/0344844 A1 | 12/2015 | Better et al. |
| 2016/0122782 A1 | 5/2016 | Crisman et al. |
| 2017/0037369 A1 | 2/2017 | Ramsborg et al. |
| 2017/0051252 A1 | 2/2017 | Morgan et al. |
| 2018/0032772 A1 | 11/2018 | Vink |
| 2018/0327722 A1 | 11/2018 | Mnk |
| 2019/0169572 A1 | 6/2019 | Shi et al. |
| 2019/0194642 A1 | 6/2019 | Smith |
| 2019/0211294 A1 | 7/2019 | Karnieli |

FOREIGN PATENT DOCUMENTS

| | | |
|---|---|---|
| EP | 0248675 A1 | 12/1987 |
| GB | 1356794 A | 6/1974 |
| JP | 2-119772 A | 5/1990 |
| JP | 2-174848 A | 7/1990 |
| JP | 3-500847 A | 2/1991 |
| JP | 5-503418 A | 6/1993 |
| JP | 6-54678 A | 3/1994 |
| JP | 6-261736 A | 9/1994 |
| JP | 7-501206 A | 2/1995 |
| JP | H08-56646 A | 3/1996 |
| JP | H11-507229 A | 6/1999 |
| JP | 2001-275659 A | 10/2001 |
| JP | 2001-517428 A | 10/2001 |
| JP | 2002-500004 A | 1/2002 |
| KR | 20000023786 U | 9/2001 |
| WO | 91/05849 A1 | 5/1991 |
| WO | 93/03142 A1 | 2/1993 |
| WO | 1997/12960 A2 | 4/1997 |
| WO | 99/33951 A1 | 7/1999 |
| WO | 99/47922 A2 | 9/1999 |
| WO | 2000/046349 A1 | 8/2000 |
| WO | 01/02030 A2 | 1/2001 |
| WO | 2001/000783 A2 | 1/2001 |
| WO | 2002/028996 A1 | 4/2002 |
| WO | 02/088295 A1 | 11/2002 |
| WO | 03/022985 A2 | 3/2003 |
| WO | 03/087292 A2 | 10/2003 |
| WO | 2003/085101 A1 | 10/2003 |
| WO | 2015/162211 A1 | 10/2015 |
| WO | 2016/069993 A1 | 5/2016 |
| WO | 2016/118780 A1 | 7/2016 |
| WO | 2016/168275 A1 | 10/2016 |
| WO | 2017/068425 A1 | 4/2017 |
| WO | 2017/129822 A1 | 8/2017 |
| WO | 2018/015561 A1 | 1/2018 |
| WO | 2018/136566 A1 | 7/2018 |

OTHER PUBLICATIONS

Farndale "Pulsed Electromagnetic Fields Promote Collagen Production in Bone Marrow Fibroblasts via Athermal Mechanisms" Calcif Tissue Int (1985) 37:178-182.

Shi et al., Performance of Mammalian Cell Culture Bioreactor with a New Impeller Design, Biotechnology and Bioengineering, Jun. 20, 1992, pp. 260-270, vol. 40, John Wiley & Sons, Inc.

Declaration from Mark Selker, Submitted in *Lonza Walkersville, Inc.* v. *Adva Biotechnology LTD.*, United States District Court for the District of Maryland, Case No. 8:20-cv-03099-PX, Jan. 5, 2022.

Declaration from James C. Leung, Submitted in *Lonza Walkersville, Inc.* v. *Adva Biotechnology LTD.*, United States District Court for the District of Maryland, Case No. 8:20-cv-03099-PX, Jan. 7, 2022.

Aitken-Christie et al., Automation in Plant tissue culture—general introduction and overview, in Automation and Environmental Control in Plant Tissue Culture 757 (J. Aitken-Christie, T. Kozai & M. Lila Smith eds., 1995).

Apel et al., Integrated Clinical Scale Manufacturing System for Cellular Products Derived by Magnetic Cell Separation, Centrifugation and Cell Culture, Chemie Ingenieur Technik (2013).

Armstrong et al., Clinical Systems for the Production of Cells and Tissues for Human Therapy, in Novel Therapeutics From Modern Biotechnology 221 (D.L. Oxender et al. eds., 1999).

Blaeschke et al., Induction of A Central Memory and Stem Cell Memory Phenotype in Functionally Active CD4+ and CD8+ Car T Cells Produced in an Automated Good Manufacturing Practice System for the Treatment of CD19+ Acute Lymphoblastic Leukemia, Cancer Immunology, Immunotherapy vol. 67, pp. 1053-1066 (2018), published Mar. 31, 2018.

Bohnenkamp et al., Bioprocess development for the cultivation of human T-lymphocytes in a clinical scale, Cytotechnology (2002).

Bousso, T-cell activation by dendritic cells in the lymph node: lessons from the movies, 8 Nature Reviews Immunology 675 (2008) ("Bousso 2008").

Kaiser et al., Towards a Commercial Process for the Manufacture of Genetically Modified T Cells for Therapy, 22 Cancer Gene Therapy 72-78 (2015).

Kempner et al., A Review of Cell Culture Automation, 7 Journal of the Association for Laboratory Automation 56 (2002) ("Kempner 2002").

Koller et al., Clinical-scale human umbilical cord blood cell expansion in a novel automated perfusion culture system, Bone Marrow Transplantation (1998) ("Koller 1998").

Koller et al., Large-Scale Expansion of Human Stem and Progenitor Cells from Bone Marrow Mononuclear Cells in Continuous Perfusion Cultures, Blood (1993) ("Koller 1993A").

Koller et al., Tissue Engineering: Reconstitution of Human Hematopoiesis Ex Vivo, Biotechnology and Bioengineering (1993) ("Koller 1993B").

Kostov et al., Low-Cost Microbioreactor for High-Throughput Bioprocessing, 72 Biotechnology and Bioengineering, Feb. 5, 2001 ("Kostov 2001").

Krug et al., A GMP-compliant protocol to expand and transfect cancer patient T cells with mRNA encoding a tumor-specific chimeric antigen receptor, Cancer Immunol Immunotherapy (2014) ("Krug 2014").

Levine et al., Global Manufacturing of Car T Cell Therapy, 4 Molecular Therapy: Methods & Clinical Development 92 (2017).

Lock et al., Automated Manufacturing of Potent CD20-Directed Chimeric Antigen Receptor T Cells for Clinical Use, 28 Human Gene Therapy 10 (2017), ("Lock 2017").

(56) References Cited

OTHER PUBLICATIONS

Lu et al., A Rapid Cell Expansion Process for Production of Engineered Autologous CART Cell Therapies, 27 Human Gene Therapy 6 (2016).
Mock et al., Automated manufacturing of chimeric antigen receptor T cells for adoptive immunotherapy using CliniMACS Prodigy, Cytotherapy (2016).
Morse, Technology evaluation: Stem-cell therapy, Aastrom Biosciences Inc., Current Opinion in Molecule Therapeutics (1999) ("Morse 1999").
Oh et al., Frequent Harvesting from Perfused Bone Marrow Cultures Results in Increased Overall Cell and Progenitor Expansion, Biotechnology and Bioengineering (1994).
Priesner et al., Automated Enrichment, Transduction, and Expansion of Clinical-Scale CD62L+ T Cells for Manufacturing of Gene Therapy Medicinal Products, 27 Human Gene Therapy 10, 860-869 (2016).
Rosazza et al., Gene Electrotransfer: A Mechanistic Perspective, Current Gene Therapy (2016) ("Rosazza 2016").
Shi et al., "Performance of Mammalian Cell Culture Bioreactor with a New Impeller Design" Biotechnology and Bioengineering, vol. 40, pp. 260-270 (1992).
Stiff et al., Autologous transplantation of ex vivo expanded bone marrow cells grown from small aliquots after high-dose chemotherapy for breast cancer, Blood (2000) ("Stiff 2000").
Wang et al., Clinical Manufacturing of Car T Cells: Foundation of a Promising Therapy, 3 Molecular Therapy—Oncolytics 1 (2016).
Wang et al., Manufacture of Tumor- and Virus-specific T Lymphocytes for Adoptive Cell Therapies, 22 Cancer Gene Therapy 2 (2015).
Zhang et al., Characterization of clinical grade CD19 chimeric antigen receptor T cells produced using automated CliniMACS Prodigy system, Drug Design, Development and Therapy (2018) ("Zhang 2018").
Zhu et al., Closed-system manufacturing of CD19 and dual-targeted CD20/19 chimeric antigen receptor T cells using the CliniMACS Prodigy device at an academic medical center, Cytotherapy (2018).
Brady J. et al., Development, Scale-Up and Technology Transfer for Rapid, Automated, cGMP Compliant, Large-Volume Suspension Cell Based Process for Lentiviral Vector Production. Mol. Ther., May 31, 2010, vol. 18, No. S1, pp. S263-S264.
Sheu J3 et al., Large-scale production of lentiviral vector in a closed system hollow fiber bioreactor. Mol Ther Methods Clin Dev, Jun. 17, 2015, vol. 2, p. 15020: 1-7 p. 5-7.
Stornaiuolo A. et al., A New Strategy for Retroviral Vector Purification Based on LNGR-Ab Immunomagnetic Selection. Mol. Ther., May 31, 2013, vol. 21, No. S1, pp. S201.
Andris et al., "Naïve T Cells are Resistant to Anergy Induction by Anti-CD3 Antibodies," The Journal of Immunology (2004) 173(5):3201-3208.
Atkuri et al., "Culturing at atmospheric oxygen levels impacts lymphocyte function," PNAS (2005) 102(10):3756-3759.
Austyn et al., "T cell activation by anti-CD3 antibodies: function of Fc receptors on B cell blasts, but not resting B cells, and CD18 on the responding T cells." European Journal of Immunology (1987) 17(9):1329-1335.
Avgoustiniatos et al., "Commercially Available Gas-Permeable Cell Culture Bags May Not Prevent Anoxia in Cultured or Shipped Islets," Transplant Proc. (2008) 40(2):395-400.
Baroja et al., "The anti-T cell monoclonal antibody 9.3 (Anti-CD28) provides a helper signal and bypasses the need for accessory cells in T Cell activation with immobilized anti-CD3 and mitogens," Cellular Immunology (1989) 120(1):205-217.
Berdeja et al., "First-in-human multicenter study of bb2121 anti-BCMA CAR T-cell therapy for relapsed/refractory multiple myeloma: Updated results," Journal of Clinical Oncology (2017) 35(15):3010.
Bohnenkamp et al., "Bioprocess development for the cultivation of human T-lymphocytes in a clincal scale," Cytotechnology (2002) 38:135-145.

Carpenter et al., "Non-Fc Receptor-Binding Humanized Anti-CD3 Antibodies Induce Apoptosis of Activated Human T Cells," The Journal of Immunology (2000) 165(11):6208-6213.
Ceuppens et al., "T cell unresponsiveness to the mitogenic activity of OKT3 antibody results from a deficiency of monocyte Fc gamma receptors for murine IgG2a inability to cross-link the T3-Ti complex," The Journal of Immunology (1985) 135(6):3882-3886.
Tordo, Julie et al., Brain, Jul. 2018, vol. 141, No. 7, pp. 2014-2031, DOI: 10.1093/brain/awy 126.
Zhou, Heshon and Beaudet, Arthur L., Virology, Sep. 30, 2000, vol. 275, Issue 2, pp. 348-357, DOI: 10.1006/viro.2000.0515.
Machitani, Mitsuhiro et al., Journal of Controlled Release, Sep. 25, 2011, vol. 154, Issue 3, pp. 285-289, DOI: 10.1016/j.jconrel.2011.06.020.
Wu et al., Common knowledge 1: Tissues Engineering of Skin, Beijing: People's Military Medical Press, Jun. 2009, pp. 306-308.
Chai et al., "Immobilized anti-CD3 mAb induces anergy in murine naïve and memory CD4+ T cells in vitro.," Int Immunol. (1997) 9(7):935-944.
Clark et al., "Cell Lines for the Production of Recombinant Adeno-Associated Virus," Human Gene Therapy 6:1329-1341 (1995).
Clavreul et al., "Interelationship between CD3 and CD28 pathways in a murine T cell thymoma," Molecular Immunology (2000) 37(10):571-577.
Dudley et al., "Generation of Tumor-Infiltrating Lymphocyte Cultures for Use in Adoptive Transfer Therapy for Melanoma Patients," J Immunother. (2003) 26(4):332-342.
Fathman et al., "Molecular mechanisms of CD4+ T-cell anergy," Nature Reviews Immunology (2007) 7:599-609.
FDA, Available online at: https://www.fda.gov/downloads/AdvisoryCommittees/CommitteesMeetingMaterials/Drugs/OncologicDrugsAdvisoryCommittee/UCM566166.pdf.
FDA, Regenerative Medicine Advanced Therapy Designation. (2017). Available at: https://www.fda.gov/BiologicsBloodVaccines/CellularGeneTherapyProducts/ucm537670.htm. (Accessed: Aug. 8, 2017).
FDA, Sepax Cell Separation System and single use kits. (2011). Available at: https://www.fda.gov/downloads/BiologicsBloodVaccines/BloodBloodProducts/ApprovedProducts/SubstantiallyEquivalent510kDeviceInformation/UCM278385.pdf. (Accessed: Nov. 8, 2017).
Feldmann et al., "Novel humanized and highly efficient bispecific antibodies mediate killing of prostate stem cell antigen-expressing tumor cells by CD8+ and CD4+ T cells," J Immunol. (2012) 189(6):3249-3259.
Fleischer et al., "Differential expression and function of CD80 (B7-1) and CD86 (B7-2) on human peripheral blood monocytes," Immunology (1996) 89(4):592-598.
Graham et al., "A New Technique for the Assay of Infectivity of Human Adenovirus 5 DNA," Virology, 52(2): 456-457 (1973).
Gottschalk et al., The hype, hope and reality of personalization. The Medicine Maker (2015) p. 38-41.
Greenwald et al., "The B7 Family Revised," Annual Review of Immunology (2005) 23:515-548.
Grishagin, Ivan V., "Automatic cell counting with ImageJ," Analytical Biochemistry (2015) 473:63-65.
Guido et al., "Human bocavirus: Current knowledge and future challenges," World J. Gateroenterol (2016) 22:8684-8697.
Hammill et al., "Designed ankyrin repeat proteins are effective targeting elements for chimeric antigen receptors," Journal for Immuno Therapy of Cancer (2015) 3(55):1-11.
Harding et al., "CD28-mediated signalling co-stimulates murine T cells and prevents induction of anergy in T-cell clones," Nature (1992) 356:607-609.
Hasegawa et al., "*In vitro* Stimulation of CD8 and CD4 T Cells by Dendritic Cells Loaded with a Complex of Cholesterol-Bearing Hydrophobized Pullulan and NY-ESO-1 Protein: Identification of a New HLA-DR15-Binding CD4 T-Cell Epitope," Clinical Cancer Research (2006) 12(6):1921-1927.
Hollyman et al., "Manufacturing validation of biologically functional T cells targeted to CD19 antigen for autologous adoptive cell therapy," J Immunother. (2009) 32(2):169-180.

(56) References Cited

OTHER PUBLICATIONS

Ishibashi et al., "Adenoviruses of animals," The Adenoviruses, Ginsberg, ed., Plenum Press, New York, N.Y., pp. 497-562 (1984).
Ju et al., "A functional anti-human 4-1BB ligand monoclonal antibody that enhances proliferation of monocytes by reverse signaling of 4-1BBL," Hybrid Hybridomics (2003) 22(5):333-338.
Kaiser et al., "Towards a commercial process for the manufacture of genetically modified T cells for therapy," Cancer Gene Therapy (2015) 22:72-78.
Kalos et al., "T Cells with Chimeric Antigen Receptors Have Potent Antitumor Effects and Can Establish Memory in Patients with Advanced Leukemia," Sci Transl Med. (2011) 3(95):1-21.
Kebriaei et al., "Phase I trials using *Sleeping Beauty* to generate CD19-specific Car T cells," The Journal of Clinical Investigation (2016) 126(9):3363-3376.
Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor," Journal of Clinical Oncology (2016) 33(6):540-549.
Kotin, R. M., "Prospects for the Use of Adeno-Associated Virus as a Vector for Human Gene Therapy," Human Gene Therapy 5:793-801 (1994).
Lafferty et al., "A new analysis of allogeneic interactions," Aust J Exp Biol Med Sci. (1975) 53(1):27-42.
Laux et al., "Response Differences between Human CD4+ and CD8+ T-Cells during CD28 Costimulation: Implications for Immune Cell-Based Therapies and Studies Related to the Expansion of Double-Positive T-Cells during Aging," Clinical Immunology (2000) 96(3):187-197.
Ledbetter et al., "CD28 Ligation in T-cell Activation: Evidence for Two Signal Transduction Pathways," Blood (1990) 75(7):1531-1539.
Levine et al., "Global Manufacturing of Car T Cell Therapy," Molecular: Therapy: Methods & Clinical Development (2017) 4:92-101.
Li et al., "Comparison of anti-CD3 and anti-CD28-coated beads with soluble anti-CD3 for expanding human T cells: Differing impact on CD8 T cell phenotype and responsiveness to restimulation," Journal of Translational Medicine (2010) 8(104):1-15.
Li et al., "Role for Highly Regulated rep Gene Expression in Adeno-Associated Virus Vector Production," Journal of Virology 71:5236-5243 (1997).
Lock et al., "Automated Manufacturing of Potent CD20-Directed Chimeric Antigen Receptor T Cells for Clinical Use," Human Gene Therapy (2017) 28(10):914-925.
Locke et al., "Abstract CT019: Primary results from ZUMA-1: a pivotal trial axicabtagene ciloleucel (axicel; KTE-C19) in patients with refractory aggressive non-Hodgkin lymphoma (NHL)," Cancer Research (2017) 77(13).
Locke et al., "Phase 1 Results of ZUMA-1: A Multicenter Study of KTE-C19 Anti-CD19 CAR T Cell Therapy in Refractory Aggressive Lymphoma," Molecular Therapy (2017) 25(1):285-295.
Lu et al., "A Rapid Cell Expansion Process for Production of Engineered Autologous CAR-T Cell Therapies," Human Gene Therapy Methods (2016) 27(6):209-218.
Lu et al., "Automated dynamic fed-batch process and media optimization for high productivity cell culture process development," (2013) 110(1):191-205.
Lu et al., "Treatment of Patients with Metastatic Cancer Using a Major Histocompatibility Complex Class II-Restricted T-Cell Receptor Targeting the Cancer Germline Antigen MAGE-A3," Journal of Clinical Oncology (2017) 35(29):3322-3329.
Mock et al., "Automated manufacturing of chimeric antigen receptor T cells for adoptive immunotherapy using CliniMACS Prodigy," Cytotherapy (2016) 18(8):1002-1011.
Morrissey et al., "End-to-End Cell Therapy Automation: An Immunotherapy Case Study," BioPharm International (2017) 2:10-18.
Mullick et al., "The cumate gene-switch: a system for regulated expression in mammalian cells," BMC Biotechnology 6:43 (1-18) (2006).
Muzyczka, N., "Use of Adeno-Associated Virus as a General Transduction Vector for Mammalian Cells," Current Topics in Microbiol. and Immunol. 158:97-129 (1992).
Nilsson et al., "Optimal Blood Mononuclear Cell Isolation Procedures for Gamma Interferon Enzyme-Linked Immunospot Testing of Healthy Swedish and Tanzanian Subjects," Clinical and Vaccine Immunology (2008) 15(4):585-589.
Nociari et al., "A novel one-step, highly sensitive fluorometric assay to evaluate cell-mediated cytotoxicity," Journal of Immunological Methods (1998) 213(2):157-167.
Odeleye et al., "On the fluid dynamics of a laboratory scale single-use stirred bioreactor," Chemical Engineering Science (2014) 111(100):299-312.
Reusch et al., "A tetravalent bispecific TandAb (CD19/CD3), AFM11, efficiently recruits T cells for the potent lysis of CD19+ tumor cells," MAbs (2015) 7(3):584-604.
Riddell et al., "Adoptive Therapy with Chimeric Antigen Receptor Modified T Cells of Defined Subset Composition," Cancer J (2014) 20(2):141-144.
Riddell et al., "The use of anti-CD3 and anti-CD28 monoclonal antibodies to clone and expand human antigen-specific T cells," Journal of Immunological Methods (1990) 128(2):189-201.
Robert et al., "Manufacturing of Recombinant Adeno-Associated Viruses Using Mammalian Expression Platforms," Biotechnology Journal 12(1600193): 1-16 (2017).
Romagnani, S, "Type 1 T helper and type 2 T helper cells: functions, regulation and role in protection and disease," Int J Clin Lab Res (1991) 21(2):152-158.
Schwartz, RH, "A cell culture model for T lymphocyte clonal anergy," Science (1990) 248(4961):1349-1356.
Schwartz, RH, "T cell anergy," Annu Rev Immunol. (2003) 21:305-334.
Strauss, "Adenovirus infections in humans," The Adenoviruses, Ginsberg, ed., Plenum Press, New York, N.Y., pp. 451-596 (1984).
Tangying et al., "A Rapid Cell Expansion Process for Production of Engineering Autologous CAR-T Cell Therapies," Human Gene Therapy Methods (2016) 27(6):209-218.
Tax et al., "Polymorphism in mitogenic effect of IgG1 monoclonal antibodies against T3 antigen on human T cells," Nature (1983) 304(5925):445:447.
Trainor et al., "Rethinking clinical delivery of adult stem cell therapies," Nature Biotechnology (2014) 32:729-735.
Trickett et al., "T cell stimulation and expansion using anti-CD3/CD28 beads," Journal of Immunological Methods (2003) 275(1-2):251-255.
Tuefferd et al., "*HER2* Status in Ovarian Carcinomas: A Multicenter GINECO Study of 320 Patients," PLoS ONE (2007) 11:e1138.
Turtle et al., "CD19 CAR-T cells of defined CD4+ :CD8+ composition in adult B cell All patients," The Journal of Clinical Investigation (2016) 126(6):2123-2138.
Urabe et al., "Insect Cells as a Factory to Produce Adeno-Associated Virus Type 2 Vectors," Human Gene Therapy 13: 193501943 (2002).
Vanseggelen et al., "Chimeric antigen receptor-engineered T cells as oncolytic virus carriers," Molecular Therapy—Oncolytics (2015) 150014.
Verwilghen et al., "Differences in the stimulating capacity of immobilized anti-CD3 monoclonal antibodies: variable dependence on interleukin-1 as a helper signal for T-cell activation," Immunology (1991) 72:269-276.
Wang et al., "Clinical manufacturing of Car T cells: foundation of a promising therapy" Mol. Ther.—Oncolytics (2016) 3:16015.
Wang et al., "Manufacture of tumor- and virus-specific T lymphocytes for adoptive cell therapies," Cancer Gene Ther. (2015) 22(2):85-94.
Wauwe et al., "OKT3: a monoclonal anti-human T lymphocyte antibody with potent mitogenic properties," The Journal of Immunology (1980) 124(6):2708-2713.
Wegener, C, "Cell Washing with the LOVO Cell Processing System," BioProcess International (2014) p. 78.

(56) References Cited

OTHER PUBLICATIONS

Weiss et al., "T cell activation: differences in the signals required for IL 2 production by nonactivated and activated T cells," J Immunol (1985) 135(6):3669-3673.

Wolf et al., "Induction of anergy in resting human T lymphocytes by immobilized anti-CD3 antibodies," European Journal of Immunology (1994) 24(6):1410-1417.

Yan et al., "HER2 expression status in diverse cancers: review of results from 37,992 patients," Cancer Metastasis Rev (2015) 34:157-164.

Yao et al., "Tetracycline Repressor, tetR, rather than the tetR-Mammalian Cell Transcription Factor Fusion Derivatives, Regulates Inducible Gene Expression in Mammalian Cells," Human Gene Therapy 9: 1939-1950 (1998).

Zhu et al., "CD137 stimulation delivers an antigen-independent growth signal for T lymphocytes with memory phenotype," Immunobiology (2007) 109(11):4882-4889.

The International Search Report issued in PCT/US2019/067354 on Apr. 30, 2020.

Charron et al., "Monocyte:T cell interaction regulates human T cell activation through a CD28/CD46 crosstalk," Immunol Cell Biol. (2015) 93(9):796-803.

Chu et al., "SV40 DNA Transfection of Cells in Suspension: Analysis of the Efficiency of Transcription and Translation of T Antigen," Gene 13(2): 197-202 (1981).

Church et al., "Tumor-specific CD4+ T cells maintain effector and memory tumor-specific CD8+ T cells," European Journal of Immunology (2014) 44:69-79.

Lonza, News Release, Oct. 29, 2018, Internet, URL: https://www.lonza.com/news/2018-10-29-19-30.

Japanese Office Action dated Jun. 25, 2024, issued is correspond JP Patent Appl. No. 2021-535876 (and English translation).

Wakitani Shigeyuki, et al., Synthesiology, vol. 6, No. 4, p. 198-208.

AUTOMATED PRODUCTION OF VIRAL VECTORS

CROSS-REFERENCE TO RELATED APPLICATIONS

The present application is a continuation of U.S. patent application Ser. No. 16/720,227, filed on Dec. 19, 2019, which claims benefit of U.S. Provisional Patent Application Nos. 62/783,589, filed Dec. 21, 2018; 62/866,092, filed Jun. 25, 2019; 62/890,904, filed Aug. 23, 2019; and 62/949,848, filed Dec. 18, 2019, the disclosures of each of which are incorporated by reference herein in their entireties.

FIELD OF THE INVENTION

The present disclosure provides an automated method of producing viral vectors, utilizing engineered viral vector-producing cell lines within a fully-enclosed cell engineering system. Exemplary viral vectors that can be produced include lentivirus vectors, adeno-associated virus vectors, baculovirus vectors and retrovirus vectors.

BACKGROUND OF THE INVENTION

Viral vectors are critically important as both basic research tools and for use in gene therapeutics. For example, the safety profile and long-term expression capacity make adeno-associated virus (AAV) an excellent viral vector for gene therapy in humans. Lentiviral vectors, similarly, are one of the most commonly used delivery methods in the field of gene and cell therapy. However, the traditional means of producing most viral vectors is expensive, time-consuming, and cumbersome. Furthermore, vector yield from methods that rely on bridging platforms (such as AAVs) or multiple transient transfections (such as lentivirus) may be too low or require too much plasmid DNA to be feasible for most therapeutic applications. In addition, for small scale viral vector production, a large batch process may not be required or desirable.

The benefits of automation of production of viral vectors include labor time savings associated with using automation as well as improved product consistency, decreased room classification, decreased clean room footprint, decreased training complexities, and improved scale-up and tracking logistics. Furthermore, software can be used to streamline the documentation processes by using automatically generated electronic batch records to provide a history of all processing equipment, reagents, operator identification, in-process sensor data, and so forth.

An automated, self-contained system in which engineered mammalian cells optimally produce viral vectors would revolutionize the field of gene therapy. There is an urgent need for technology that would allow control of viral production for large or small scale volume production, provide reproducible and stable results, while simultaneously limiting contamination and reducing cost.

SUMMARY OF THE INVENTION

In some embodiments, provided herein is a method for automated production of an adeno-associated virus (AAV) viral vector, comprising: introducing an engineered mammalian AAV viral producer cell into a fully enclosed cell engineering system, the engineering mammalian AAV viral producer cell including integrated into its genome: an adenovirus helper gene comprising E2A and E4Orf6 genes under control of a first derepressible promoter; an AAV gene comprising Rep and Cap genes under control of a second derepressible promoter; a viral-associated, non-coding RNA under control of a third derepressible promoter; and a repressor element of the first, second and third derepressible promoters; transducing the mammalian AAV viral producer cell with a vector encoding a gene of interest to produce a transduced viral producer cell; treating the mammalian AAV viral producer cell with a binding partner of the repressor element; activating the first, second and third derepressible promoters; expanding the transduced viral producer cell and producing the AAV viral vector within the transduced viral producer cell; and isolating the viral vector, wherein the steps are performed in a closed and automated process.

Also provided herein is a method for automated production of an adeno-associated virus (AAV) viral vector, comprising: transducing a mammalian cell stably expressing one or more nucleic acids encoding TetR and/or TetR-KRAB with: a first nucleic acid encoding an adenovirus helper gene comprising an E2A gene, a E4Orf gene and a viral-associated non-coding RNA, under control of a first derepressible promoter; a second nucleic acid encoding an AAV gene comprising Rep and Cap genes under control of a second derepressible promoter; and optionally, a third nucleic acid encoding a gene of interest under control of a third derepressible promoter; treating the mammalian cell with a binding partner of the TetR; activating the first, second and third derepressible promoters; expanding the transduced cell and producing the AAV viral vector within the transduced cell; and isolating the viral vector, wherein the steps are performed in a closed and automated process.

In further embodiments, provided herein is a method for automated production of a lentiviral vector, comprising: introducing an engineered mammalian lentiviral vector producer cell into a fully enclosed cell engineering system, the engineering mammalian lentiviral vector producer cell including integrated into its genome: a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the nucleic acid sequence is flanked on both the 5' and 3' ends by sequences resulting from the recombination of transposon-specific inverted terminal repeats (ITRs); transducing the mammalian lentiviral vector producer cell with a vector encoding a gene of interest to produce a transduced viral producer cell; activating the first, second and third promoters; expanding the transduced viral producer cell and producing the lentiviral vector within the transduced viral producer cell; and isolating the viral vector, wherein (a) through (e) are performed in a closed and automated process.

In further embodiments, provided herein is a method for automated production of a lentiviral vector, comprising: introducing a mammalian cell into a fully enclosed cell engineering system; transducing a mammalian cell with: a first nucleic acid encoding a lentiviral regulator of expression of virion proteins (REV) gene under control of a first promoter and an envelope glycoprotein gene under control of a second promoter; a second nucleic acid encoding a gene of interest under control of a third promoter; and a third nucleic acid encoding a lentiviral group specific antigen (GAG) gene and a lentiviral polymerase (POL) gene both under control of a fourth promoter, expanding the transduced cell and producing the lentiviral vector within the transduced cell; and isolating the viral vector, wherein the steps are performed in a closed and automated process.

DETAILED DESCRIPTION OF THE INVENTION

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the method/device being employed to determine the value. Typically, the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer only to alternatives or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited, elements or method steps. It is contemplated that any embodiment discussed in this specification can be implemented with respect to any method, system, host cells, expression vectors, and/or composition of the invention. Furthermore, compositions, systems, cells, and/or nucleic acids of the invention can be used to achieve any of the methods as described herein.

In embodiments, provided herein is a method for automated production of a viral vector. The automated methods described herein suitably take place in a fully enclosed, cell engineering system.

As described herein, "a fully enclosed cell engineering system" refers to a closed system, suitably including a plurality of chambers, and wherein each of steps of the various methods described herein are performed in the same or a different chamber of the plurality of chambers of the cell engineering system. Suitably, each of the various cells, vectors and cell culture medium, are contained in a different chamber of the plurality of the chambers prior to starting the method. The cell engineering systems suitably include one or more chambers maintained at a temperature for growing cells (e.g., at about 37° C.) and at least one of the plurality of chambers is maintained at a refrigerated temperature (e.g., at about 4-8° C.). "Fully enclosed" suitably refers to the plurality of chambers being interconnected, including via various tubing or other fluidly connected pathways and connections, to maintain the cleanness, and suitably sterility, of the fully enclosed systems.

Figure 1:
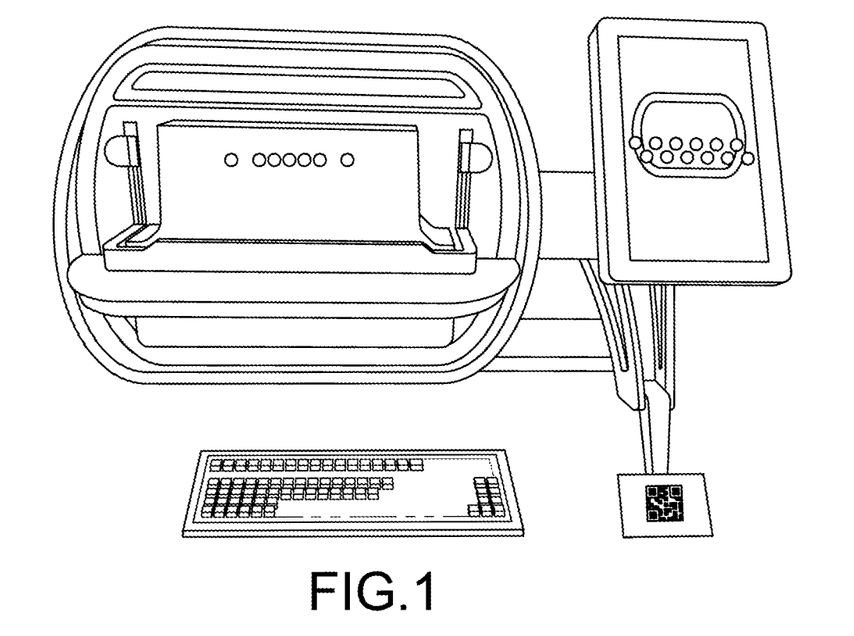
FIG. 1 shows a closed and automated system useful for producing viral vectors as described in embodiments herein.
Figure 2:
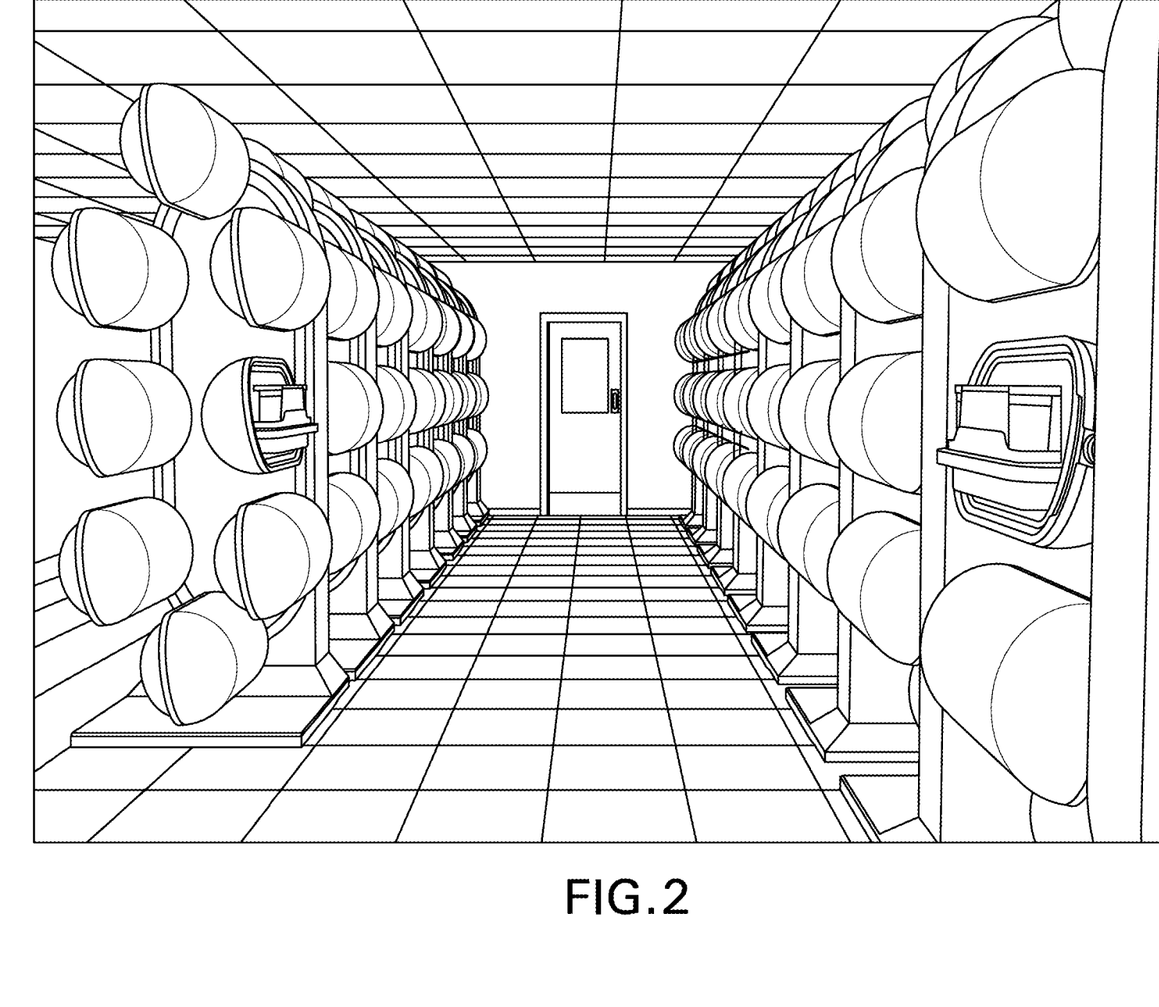
FIG. 2 shows a lab space containing exemplary closed and automated systems useful for producing viral vectors as described in embodiments herein.

As described herein, in embodiments, the methods provided utilize the COCOON platform (Octane Biotech (Kingston, ON)), which integrates multiple unit operations in a single turnkey platform. To provide efficient and effective automation translation, the methods described utilize the concept of application-specific/sponsor-specific disposable cassettes that combine multiple unit operations—all focused on the core requirements of the viral vector product. Exemplary fully enclosed cell engineering systems are described in Published U.S. Patent Application No. 2019-0169572, the disclosure of which is incorporated by reference herein in its entirety. An exemplary fully enclosed cell engineering useful in the methods described herein is shown in FIG. 1. FIG. 2 shows a lab space containing exemplary closed and automated systems useful for producing viral vectors as described in embodiments herein in a high throughput arrangement. In embodiments, each of the closed and automated systems can be producing a separate and unique viral vector.

In embodiments, the methods described herein take place in a cassette of a fully enclosed cell engineering system that can include a low temperature chamber, for storage of a cell culture media; a high temperature chamber for carrying out processes involved in producing a viral vector, wherein the high temperature chamber is separated from the low temperature chamber by a thermal barrier, the high temperature chamber including a cell culture chamber; and one or more fluidics pathways connected to the cell culture chamber, wherein the fluidics pathways provide recirculation, removal of waste and homogenous gas exchange and distribution of nutrients to the cell culture chamber without disturbing cells within the cell culture chamber.

Figure 3:
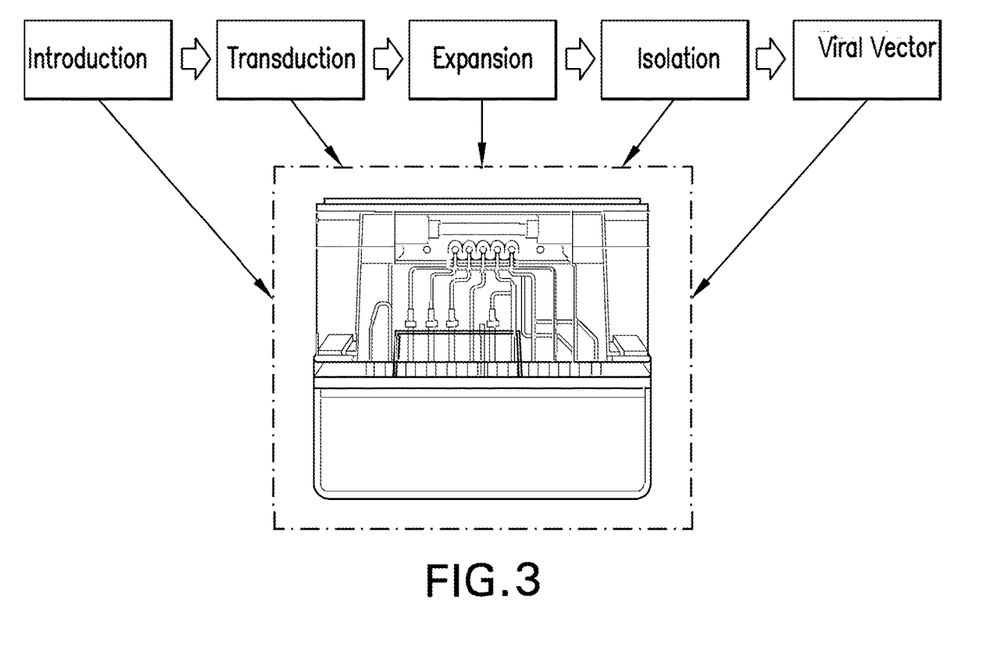
FIG. 3 shows flow diagram of a viral vector production process that can be performed in a closed and automated system as described in embodiments herein.

FIG. 3 shows a flow diagram of a viral vector production process that can be performed in a closed and automated system as described in embodiments herein, illustrating the various steps that can take place within a cartridge of a closed and automated system.

In embodiments, the methods for automated production suitably include introducing an engineered viral producer cell into the fully enclosed cell engineering system.

As referred to herein, an "engineered viral producer cell" utilized in the methods is a cell that suitably includes one or more nucleic acid molecules encoding helper genes or expression systems that allow for production of viral vectors.

As referred to herein, the word "introducing" can mean adding the engineered viral producer cell to one of a plurality of chambers, or can indicate the presence of the engineered viral producer cell within the cassette prior to beginning the method.

In embodiments, the methods described herein are configured to perform several rounds of one or more of feeding, washing and monitoring of the engineered viral producer cell. These various activities can be performed in any order and can be performed alone or in combination with another activity. In embodiments, concentrating of the cells comprises centrifugation, supernatant removal following sedimentation, or filtration. Suitably, the optimization process further includes adjusting parameters of the centrifugation or filtration, suitably in a self-adjusting process.

The methods described herein suitably further include transducing the engineered viral producer cell with a vector encoding a gene of interest to produce a transduced viral producer cell.

As referred herein, "transduction" or "transducing" means the introduction of an exogenous nucleic acid molecule, including a vector, into a cell. A "transduced" cell comprises an exogenous nucleic acid molecule inside the cell and induces a phenotypic change in the cell. The transduced nucleic acid molecule can be integrated into the host cell's genomic DNA and/or can be maintained by the cell, temporarily or for a prolonged period of time, extra-chromosomally. Host cells or organisms that express exogenous nucleic acid molecules or fragments are referred to as "recombinant," "transduced," "transfected," or "transgenic" organisms. A number of transduction and transfection techniques are generally known in the art. See, e.g., Graham et al., *Virology*, 52:456 (1973); Sambrook et al., Molecular Cloning, a laboratory manual, Cold Spring Harbor Laboratories, New York (1989); Davis et al., Basic Methods in Molecular Biology, Elsevier (1986); and Chu et al., *Gene* 13:197 (1981). Transduction can include the use of a transfection system such as a liposome, lipid-based, or polymer-based system, and can also include the use of mechanical transfection such as gene guns, electroporation, etc.

As used herein, a "vector" or "expression vector" is a replicon, such as a plasmid, phage, virus, or cosmid, to which a nucleic acid molecule described herein may be attached to bring about the replication and/or expression of the attached nucleic acid molecule in a cell. "Vector" includes episomal (e.g., plasmids) and non-episomal vectors. The term "vector" includes both viral and non-viral means for introducing a nucleic acid molecule into a cell in vitro, in vivo, or ex vivo. The term vector may include synthetic vectors. Vectors may be introduced into the desired host cells by well-known methods, including, but not limited to, transfection, transduction, cell fusion, and lipofection. Vectors can comprise various regulatory elements including promoters.

A "viral vector," as produced by the methods described herein, refers to a product virus that can be used to introduce a nucleic acid molecule into a cell in vitro, in vivo, or ex vivo, suitably for a therapeutic or industrial purpose. Viral vectors produced by the various methods described herein can be harvested or isolated, and stored until a final desired application.

A "gene" refers to an assembly of nucleotides that encode a polypeptide and includes cDNA and genomic DNA nucleic acid molecules. "Gene" also refers to a nucleic acid fragment that can act as a regulatory sequence preceding (5' non-coding sequences) and following (3' non-coding sequences) the coding sequence. In some embodiments, genes are integrated with multiple copies. In some embodiments, genes are integrated at predefined copy numbers.

As referred to herein, the term "gene of interest" or "GOI" is used to describe a heterologous gene. As referred to herein, the term "heterologous gene" or "HG" as it relates to nucleic acid sequences such as a coding sequence or a control sequence, denotes a nucleic acid sequence, e.g. a gene, that is not normally joined together, and/or are not normally associated with a particular cell. In some embodiments, a heterologous gene is a construct where the coding sequence itself is not found in nature (e.g., synthetic sequences having codons different from the native gene). Allelic variation or naturally occurring mutational events do not give rise to heterologous DNA, as used herein.

Suitably, the gene of interest is a gene of therapeutic interest. As used herein a "gene of therapeutic interest" refers to any functionally relevant nucleotide sequence. Thus, the gene of therapeutic interest of the present disclosure can comprise any desired gene that encodes a protein that is defective or missing from a target cell genome or that encodes a non-native protein having a desired biological or therapeutic effect (e.g., an antiviral function), or the sequence can correspond to a molecule having an antisense or ribozyme function. Representative (non-limiting) examples of suitable genes of therapeutic interest include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemias and hemophilia; genetic defects such as cystic fibrosis, Gaucher's Disease, adenosine deaminase (ADA) deficiency, emphysema, etc. Several antisense oligonucleotides (e.g., short oligonucleotides complementary to sequences around the translational initiation site (AUG codon) of an mRNA) that are useful in antisense therapy for cancer and for viral diseases have been described in the art and are also examples of suitable genes of therapeutic interest.

In exemplary embodiments, the methods described herein, and thus the gene of therapeutic interest, are useful in producing viral vectors for applications in ultra-rare diseases. Such diseases may not require a significant amount of viral vector (as it may be a single or a few patients, or 10's of patients, or 100's of patients, for treatment), but sterility, reproducibility and process control are extremely critical in such applications. The methods described herein utilizing a closed an automated system allow for the desire level of control of the production.

In embodiments, the methods further comprise expanding the transduced viral producer cell and producing the viral vector within the transduced viral producer cell. As described herein, the methods of expanding the transduced viral producer cells suitably include at least one or more of feeding, washing, and monitoring. "Expanding" a transduced viral producer cell refers to various methods that allow the cells to grow until they reach a pre-defined, desired culture size. The pre-defined culture size may include a sufficient number of cells that allow for the production of a suitable or desirable number of viral vectors. In some embodiments, the number of viral producer cells is about $10^5$ cells, about $10^6$ cells, about $10^7$ cells, about $10^8$ cells, about $10^9$ cells, or about $10^{10}$ cells.

The methods of production described herein suitably further include isolating the viral vector produced in the transduced viral producer cell. Methods of isolating or otherwise harvesting the viral vector include collecting the transduced and expanded viral producer cells, and can include dissolving or otherwise disrupting the cell membrane, and collecting the viral vector.

Isolation of the viral vector can also include additional steps such as centrifuging or filtering the viral producer cells, washing the cells or filtering the isolated viral vectors. Isolation suitably includes various separation techniques that can rely on filtration, centrifugation, gel purification techniques, gradient separation techniques, etc. The viral vector can be removed by washing, or by binding the vector to a surface (e.g., a retronectin or fibronectin coated surface) and then transferring the cells to a different chamber.

As described herein, the elements of the automated production method are suitably performed in a closed and automated process. The term "closed" process suitably refers to the use of a cartridge or other contained system that does not allow for interaction with the external environment (unless desired), and is suitably a sterile process. The "automated" process or "automation" of the process refers to the control of one or more process of the cell engineering system by an external control, including a microprocessor, to monitor and change the parameters based on a defined, or pre-set set of circumstances or desired characteristics.

In embodiments, the closed and automated process is a self-adjusting process, that is one that does not require input from an external (human) user and is able, via various computer programs and conditions, to determine the required modifications to a cell culture or other characteristics to optimize the automated process. In embodiments, the closed and automated process includes monitoring with one or more of a temperature sensor, a pH sensor, a glucose sensor, a lactose sensor, an oxygen sensor, a carbon dioxide sensor, and an optical density sensor. As described herein, the use of these various sensors in the fully enclosed cell engineering system occurs at various times and locations within the system and work together in concert to provide the optimization. For example, the closed and automated process can adjust (e.g., raise or lower) one or more of a temperature, a pH level, a glucose level, a lactose level, an oxygen level, a carbon dioxide level, and an optical density of the viral-producing cell culture, based on the monitoring.

The automated process can also be based on the unique characteristics of the starting cell population, including for example, the total cell number, the source of the cells, the density of the cells, the age of the cells, etc. These starting cell population characteristics can be input into a computer control system prior to beginning the automated methods, upon which the system will make various initial modifications to optimize the methods, e.g., lactose, oxygen and carbon dioxide concentration, flow rates, incubation times, pH, etc. Alternatively, the monitoring of cell processes enables the automated characterization of the progress of the cell culture sequence from the starting population to enable case-by-case adjustment of conditions for optimized final cell culture properties.

In further embodiments, the cell engineering system recirculates nutrients, waste, released cytokines, and/or dissolved gasses during the various method processes. This recirculation helps aid in the production of the desired viral vectors. Other mechanisms for optimizing the production of the viral vectors include modifying and controlling the flow rate of the media provided to the cells. As the cells begin to grow, the circulation rate of the media provided is increased, which improves gas exchange and allows oxygen and carbon dioxide to either enter or leave the cell culture, depending on the conditions of the cells and the requirements at the time.

In embodiments, the engineered viral producer cell that is utilized in the automated methods is a mammalian cell. As used herein, the term "mammalian cell" includes cells from any member of the order Mammalia, such as, for example, human cells, mouse cells, rat cells, monkey cells, hamster cells, and the like. In some embodiments, the cell is a mouse cell, a human cell, a Chinese hamster ovary (CHO) cell, a CHOK1 cell, a CHO-DXB11 cell, a CHO-DG44 cell, a CHOK1SV cell including all variants (e.g. POTELLI-GENT®, Lonza, Slough, UK), a CHOK1SV GS-KO (glutamine synthetase knockout) cell including all variants (e.g., XCEED™ Lonza, Slough, UK). Exemplary human cells include human embryonic kidney (HEK) cells, such as HEK293, HEK293T, a HeLa cell, or a HT1080 cell.

Mammalian cells include mammalian cell cultures which can be either adherent cultures or suspension cultures. Adherent cultures refer to cells that are grown on a substrate surface, for example a plastic surface, plate, dish or other suitable cell culture growth platform, and may be anchorage dependent. Suspension cultures refer to cells that can be maintained in, for example, culture flasks or large suspension vats, which allows for a large surface area for gas and nutrient exchange. Suspension cell cultures often utilize a stirring or agitation mechanism to provide appropriate mixing. Media and conditions for maintaining cells in suspension are generally known in the art. An exemplary suspension cell culture includes human HEK293 clonal cells.

In embodiments, the methods of production of a viral vector provided herein produce an adeno-associated virus (AAV) vector.

As used herein, the term "adeno-associated virus (AAV) vector" refers to a small sized, replicative-defective, nonenveloped virus containing a single stranded DNA of the family Parvoviridae and the genus Dependoparvovirus. Over 10 adeno-associated virus serotypes have been identified so far, with serotype AAV2 being the best characterized. Other non-limiting examples of AAV serotypes are ANC80, AAV1, AAV3, AAV4, AAV5, AAV6, AAV7, AAV8, AAV9, AAV10, and AAV11. In addition to these serotypes, AAV pseudotypes have been developed. An AAV pseudotype contains the capsid of a first serotype and the genome of a second serotype (e.g. the pseudotype AAV2/5 would correspond to an AAV with the genome of serotype AAV2 and the capsid of AAV5).

As referred to herein, the term "adenovirus" refers to a nonenveloped virus with an icosahedral nucleocapsid containing a double stranded DNA of the family Adenoviridae. Over 50 adenoviral subtypes have been isolated from humans and many additional subtypes have been isolated from other mammals and birds. See, e.g., Ishibashi et al., "Adenoviruses of animals," In *The Adenoviruses*, Ginsberg, ed., Plenum Press, New York, N.Y., pp. 497-562 (1984); Strauss, "Adenovirus infections in humans," In *The Adenoviruses*, Ginsberg, ed., Plenum Press, New York, N.Y., pp. 451-596 (1984). These subtypes belong to the family Adenoviridae, which is currently divided into two genera, namely Mastadenovirus and Aviadenovirus. All adenoviruses are morphologically and structurally similar. In humans, however, adenoviruses show diverging immunological properties and are, therefore, divided into serotypes. Two human serotypes of adenovirus, namely AV2 and AV5, have been studied intensively and have provided the majority of general information about adenoviruses.

In embodiments, the methods of production of viral vector provided herein produce a lentivirus vector.

As referred herein, the term "lentivirus vector" refers to an enveloped virus with a small spherical shape containing two single stranded RNA molecules belonging to the family Retroviridae. Lentiviruses contain gag, pol, and env genes and are further distinguished from other retrovirus family members by having two regulatory genes, tat and rev. Lentivirus vectors are widely known in the art as useful tools in molecular biology to induce expression of genes of interest in cultured cells and animal tissues.

In embodiments, the methods of production of viral vector provided herein produce a retrovirus vector.

As referred herein, the term "retrovirus" refers to one or more members of the family Retroviridae, which are enveloped viruses with a small spherical shape containing two single stranded RNA molecules. Retroviruses convert their RNA molecules into DNA, which is then integrated into the host genome of the infected cell. Retrovirus-based vectors are well-known in the field of gene therapy for cancer treatment where immune cells are re-programmed to target and destroy cancer cells.

In embodiments, the methods of production of viral vector provided herein produce a baculovirus vector.

As referred herein, the term "baculovirus" refers to one or more members of the family Baculoviridae that are rod-shaped viruses containing a circular dsDNA and are known to primarily infect and replicate within insect larvae. Baculovirus expression vector systems are well-established and highly useful for the production of proteins in eukaryotic cells (Summers et al., 2006).

In additional embodiments, the methods suitably utilize an insect cell as the viral producer cell. As referred to herein, an "insect cell" suitably refers to cells that originate from insects such as but not limited to members of the lepidopteran order used for expression and manufacture of proteins and/or baculovirus vector production.

In embodiments, the methods suitably utilize an Sf9 cell. As referred here, an "Sf9 cell" is an insect cell line derived from pupal ovarian tissue of the worm *Spodoptera frugiperda*, commonly used for expression and manufacture of proteins and/or baculovirus vector production.

In embodiments, an amount of viral vector produced by the methods described herein is at least about $10^{10}$ viral vectors. For example, the amount of viral vectors produced by the methods described herein is at least about $10^{10}$ viral vectors, or at least about $10^{11}$ viral vectors, or at least about $10^{12}$ viral vectors, or at least about $10^{13}$ viral vectors, or at least about $10^{14}$ viral vectors, or about $10^{10}$-$10^{14}$ viral vectors, or about $10^{10}$-$10^{13}$ viral vectors, or about $10^{10}$-$10^{12}$ viral vectors, or about $10^{10}$, about $10^{11}$, about $10^{12}$, or about $10^{13}$ viral vectors.

In embodiments, the methods described herein are for production of an adeno-associated virus (AAV) viral vector. Such processes suitably comprise introducing an engineered mammalian AAV viral producer into a fully enclosed cell engineering system. The AAV viral producer cell suitably includes, integrated into its genome, an adenovirus helper gene comprising E2A and E4Orf6 genes under control of a first derepressible promoter.

Exemplary engineered mammalian AAV viral producer cells suitably utilized in the methods to produce an AAV viral vector are described in detail in U.S. provisional applications 62/783,589, filed Dec. 21, 2018, and 62/866,092, filed Jun. 25, 2019, and U.S. Nonprovisional patent application Ser. No. 16/719,251, filed Dec. 18, 2019, the disclosures of each which are hereby incorporated by reference in their entireties.

As described herein, suitably the mammalian AAV viral producer cells utilized in the methods include a nucleic acid molecule encoding a viral helper gene. Viral helper genes include various adenoviral virus genes, herpes virus genes and bocavirus genes (see, e.g., Guido et al., "Human bocavirus: Current knowledge and future challenges," *World J. Gateroenterol* 22:8684-8697, the disclosure of which is incorporated by reference herein in its entirety). In exemplary embodiments, the viral helper gene is an adenovirus helper gene. As referred to herein, the term "adenovirus helper gene" or "AV helper gene" refers to a gene that is composed of one or more nucleic acid sequences derived from one or more adenovirus subtypes or serotypes that contributes to Adeno-associated virus replication and packaging. In some embodiments, the Adenovirus helper gene is E1A, E1B, E2A, E4 (including E4Orf6), VA, or a combination thereof or any other adenovirus helper gene. In exemplary embodiments, the adenovirus helper gene comprises both E2A and E4Orf6 genes. Suitably, an internal ribosome entry site (IRES) element is included between the E2A and E4Orf6 genes. The IRES element initiates translation of the E4Orf6 gene after the E2A gene in a single expression cassette, providing stability to the construct.

Suitably, the promoters used to control the transcription of the various genes for producing the AAV viral vectors are derepressible promoters. As used herein, a "derepressible promoter" refers to a structure that includes a functional promoter and additional elements or sequences capable of binding to a repressor element to cause repression of the functional promoter. "Repression" refers to the decrease or inhibition of the initiation of transcription of a downstream coding or non-coding gene sequence by a promoter.

In further embodiments, the method of automated production of an AAV viral vector comprises an engineered mammalian viral producer cell that contains an AAV gene comprising Rep and Cap genes under control of a second derepressible promoter.

As referred to herein, the term "Rep" gene refers to the art-recognized region of the AAV genome which encodes the replication proteins of the virus which are collectively required for replicating the viral genome, or functional homologues thereof such as the human herpesvirus 6 (HHV-6) rep gene which is also known to mediate AAV-2 DNA replication. Thus, the rep coding region can include the genes encoding for AAV Rep78 and Rep68 (the "long forms of Rep"), and Rep52 and Rep40 (the "short forms of Rep"), or functional homologues thereof. The rep coding region, as used herein, can be derived from any viral serotype, such as the AAV serotypes described herein. The region need not include all wild-type genes but may be altered, (e.g., by insertion, deletion or substitution of nucleotides), so long as the rep genes present provide for sufficient integration functions when expressed in a suitable target cell. See, e.g. Muzyczka, N., *Current Topics in Microbiol. and Immunol.* 158:97-129 (1992); and Kotin, R. M., *Human Gene Therapy* 5:793-801 (1994).

As referred to herein, the term "Cap" gene refers to the art-recognized region of the AAV genome which encodes the capsid proteins of the virus. Illustrative (non-limiting) examples of these capsid proteins are the AAV capsid proteins VP1, VP2, and VP3. Cap genes used in this disclosure can come from any AAV serotype or a combination of AAV serotypes.

In further embodiments, the AAV viral producer cell can contain a viral-associated, non-coding RNA under control of a third derepressible promoter.

In further embodiments, the method utilizes an AAV viral producer cell that contains a repressor element of the first, second and third derepressible promoters.

As referred to herein, a "repressor element" refers to a protein or polypeptide that is capable of binding to a promoter (or near a promoter) so as to decrease or inhibit the activity of the promoter. A repressor element can interact with a substrate or binding partner of the repressor element, such that the repressor element undergoes a conformation change. This conformation change in the repressor element takes away the ability of the repressor element to decrease or inhibit the promoter, resulting in the "derepression" of the promoter, thereby allowing the promoter to proceed with the initiation of transcription. A "functional promoter" refers to a promoter, that absent the action of the repressor element, would be capable of initiating transcription. Various functional promoters that can be used in the practice of the present invention are known in the art, and include for example, $P_{CMV}$, $P_{H1}$, P19, P5, P40 and promoters of Adenovirus helper genes (e.g., E1A, E1B, E2A, E4Orf6, and VA).

In embodiments, the method suitably comprises transducing the mammalian AAV viral producer cell with a vector encoding a gene of interest to produce a transduced viral producer cell.

In embodiments, the method further comprises treating the mammalian AAV viral producer cell with a binding partner of the repressor element.

Exemplary repressor elements and their corresponding binding partners that can be used as derepressible promoters are known in the art, and include systems such as the cumate gene-switch system (CuO operator, CymR repressor and cumate binding partner) (see, e.g., Mullick et al., "The cumate gene-switch: a system for regulated expression in mammalian cells," *BMC Biotechnology* 6:43 (1-18) (2006), the disclosure of which is incorporated by reference herein in its entirety, including the disclosure of the derepressible promoter system described therein) and the TetO/TetR system described herein (see, e.g., Yao et al., "Tetracycline Repressor, tetR, rather than the tetR-Mammalian Cell Transcription Factor Fusion Derivatives, Regulates Inducible Gene Expression in Mammalian Cells," *Human Gene Therapy* 9:1939-1950 (1998), the disclosure of which is incorporated by reference herein in its entirety).

In further embodiments, the method comprises activating the first, second and third derepressible promoters.

In further embodiments, the method suitably comprises expanding the transduced viral producer cell and producing the AAV viral vector and subsequently isolating the viral vector.

In embodiments, the steps of the method are performed in a closed and automated process.

In further embodiments, provided herein is a method for automated production of an adeno-associated virus (AAV) viral vector, comprising: transducing a mammalian cell stably expressing one or more nucleic acids encoding TetR and/or TetR-KRAB with: a first nucleic acid encoding an adenovirus helper gene comprising an E2A gene, a E4Orf gene and a viral-associated non-coding RNA, under control of a first derepressible promoter; a second nucleic acid encoding an AAV gene comprising Rep and Cap genes under control of a second derepressible promoter; and optionally, a third nucleic acid encoding a gene of interest under control of a third derepressible promoter; treating the mammalian cell with a binding partner of the TetR; activating the first, second and third derepressible promoters; expanding the transduced cell and producing the AAV viral vector within the transduced cell; and isolating the viral vector, wherein the steps are performed in a closed and automated process.

In embodiments, the cell, including the engineered mammalian AAV viral producer cell, utilized in the methods of production is a mammalian cell culture, which, in some embodiments, suitably is a suspension culture. Exemplary mammalian cells include CHO cells or human cells, including HEK cells.

In further embodiments, the methods of automated production of an AAV viral vector suitably utilizes derepressible promoters that comprise a functional promoter and two tetracycline operator sequences (TetO$_2$). In such embodiments, the repressor element is a tetracycline repressor protein.

In exemplary embodiments, as described herein, the derepressible promoters comprise a functional promoter and two tetracycline operator sequences (TetO$_2$). Upon binding of two tetracycline repressor proteins (TetR—the repressor elements for the TetO$_2$ sequences), to the TetO$_2$ sequences, little or no transcription takes place from these promoters. Upon binding of a binding partner for TetR (suitably Doxycycline (Dox)), the TetR proteins change conformation, release from the TetO$_2$ sequences, and the functional promoters begin their normal transcription processes, as they would naturally. Thus, in embodiments, the method of automated production suitably further comprises treating the cells with doxycycline, which activates the derepressible promoters, allowing for production of the viral vectors In embodiments, the methods of automated production of an AAV viral vector comprises the gene of interest being a gene of therapeutic interest.

In embodiments, the methods of automated production of an AAV viral vector produces at least about $10^{10}$ viral vectors. For example, the amount of AAV viral vectors produced by the methods described herein is at least about $10^{10}$ AAV viral vectors, or at least about $10^{11}$ AAV viral vectors, or at least about $10^{12}$ AAV viral vectors, or at least about $10^{13}$ AAV viral vectors, or at least about $10^{14}$ AAV viral vectors, or about $10^{10}$-$10^{14}$ AAV viral vectors, or about $10^{10}$-$10^{13}$ AAV viral vectors, or about $10^{10}$-$10^{12}$ AAV viral vectors, or about $10^{10}$, about $10^{11}$, about $10^{12}$, or about $10^{13}$ AAV viral vectors.

In additional exemplary embodiments, the method disclosed is a method for automated production of a lentiviral vector, comprising introducing an engineered mammalian lentiviral vector producer cell into a fully enclosed cell engineering system. Methods for producing a lentiviral vector producer cell are found in U.S. Provisional Patent Application No. 62/890,904, filed Aug. 23, 2019, the disclosure of which is incorporated by reference herein in its entirety.

As used herein a "lentiviral vector producer cell" refers to a cell that contains, integrated into its genome, the elements required to produce a lentiviral vector.

In embodiments, the method utilizes a lentiviral vector producer cell including integrated into its genome a lentiviral regulator of expression of virion proteins (REV) gene under control of a first promoter, a lentiviral envelope gene (an envelope glycoprotein gene) under control of a second promoter, and a lentiviral group specific antigen (GAG) gene and a lentiviral polymerase (POL) gene both under control of a third promoter. In suitable embodiments, the nucleic acid sequence is flanked on both the 5' and 3' ends by sequences resulting from the recombination of transposon-specific inverted terminal repeats (ITRs).

As disclosed herein, the lentiviral regulator of expression of virion proteins (REV) is an RNA-binding protein that promotes late phase gene expression. It is also important for the transport of the unspliced or singly-spliced mRNAs, which encode viral structural proteins, from the nucleus to the cytoplasm.

The envelope glycoprotein gene, suitably a Vesicular Somatitis Virus Glycoprotein (VSV-G) gene, is expressed and displayed on the surface of lentiviral vectors and mediates the transduction of lentiviral vector into the target cells.

GAG encodes a polyprotein that is translated from an unspliced mRNA which is then cleaved by the viral protease (PR) into the matrix protein, capsid, and nucleocapsid proteins. The lentiviral polymerase (POL) is expressed as a GAG-POL polyprotein as a result of ribosomal frameshifting during GAG mRNA translation, and encodes the enzymatic proteins reverse transcriptase, protease, and integrase. These three proteins are associated with the viral genome within the virion. Suitably the GAG gene is an HIV GAG gene and the POL gene is an HIV POL gene.

In suitable embodiments, the expression cassette is flanked on both the 5' and 3' ends by transposon-specific inverted terminal repeats (TTR).

Exemplary promoters for use in the lentiviral vector-producing cells are known in the art and include derepressible promoters, and suitably the expression cassette further encodes a repressor element of the first, second and third derepressible promoters. In embodiments, the derepressible promoters comprises a functional promoter and a tetracycline operator sequence (TetO), and the repressor element is a tetracycline repressor protein, as described herein.

In further embodiments, the method to produce a lentiviral vector includes transducing the mammalian lentiviral vector producer cell with a vector encoding a gene of interest. In embodiments, the gene of interest is a gene of therapeutic interest.

In further embodiments, the method includes activation of the first, second, and third promoters within the lentiviral vector producer cell and expanding the transduced viral producer cell.

In further embodiments, the method includes suitably isolating the produced lentiviral vector. Methods for isolated produced viral vectors are described herein.

In exemplary embodiments, the method is performed in a closed an automated process.

In further embodiments, methods are provided for automated production of a lentiviral vector, comprising: introducing a mammalian cell into a fully enclosed cell engineering system; transducing a mammalian cell with: a first nucleic acid encoding a lentiviral regulator of expression of virion proteins (REV) gene under control of a first promoter and an envelope glycoprotein gene under control of a second promoter; a second nucleic acid encoding a gene of interest under control of a third promoter; and a third nucleic acid encoding a lentiviral group specific antigen (GAG) gene and a lentiviral polymerase (POL) gene both under control of a fourth promoter, expanding the transduced cell and producing the lentiviral vector within the transduced cell; and isolating the viral vector, wherein (a) through (d) are performed in a closed and automated process. Methods for production of transient production of lentiviral vectors can be found in U.S. Provisional Patent Application No. 62/949,848, filed Dec. 18, 2019, the disclosure of which is incorporated by reference herein in its entirety.

As described herein, suitably the automated methods utilize a mammalian cell that is a mammalian cell culture, and in embodiments is a suspension culture. Exemplary cells include human cells such as HEK293 or HEK293T cells.

In further embodiments, the methods utilize a nucleic acid that comprises a Kruppel-associated box (KRAB) sequence following a sequence encoding the tetracycline repressor protein.

As described herein, suitably a KRAB sequence (approximately 75 amino acids) is a transcriptional repression domain from the human zinc finger protein 10, and provides increased regulation of the repressor element, suitably the TetR repressor element. The KRAB domain functions as a transcriptional repressor when tethered to the template DNA by a DNA-binding domain.

In further embodiments, the methods provided herein further comprise transposon-specific ITRs that are Lepidopteran transposon (PIGGYBAC®) ITRs.

Transposable elements (transposons) can move around a genome of a cell and are useful for inserting genes for the production of transgenic organisms. The Lepidopteran transposon PIGGYBAC® is capable of moving within the genomes of a wide variety of species, and is useful in gene transduction vectors. The transposon structure includes a complex repeat configuration consisting of an internal repeat (IR), a spacer, and a terminal repeat (TR) at both ends, and a single open reading frame encoding a transposase.

Exemplary Lepidopteran transposon (PIGGYBAC®) ITRs that can be used in the plasmids and expression cassettes described herein include those disclosed in U.S. Pat. No. 7,105,343, the disclosure of which is incorporated by reference herein in its entirety.

In embodiments, the method of automated production of a lentiviral viral vector produces at least about $10^{10}$ viral vectors. For example, the amount of lentiviral vectors produced by the methods described herein is at least about $10^{10}$ lentiviral vectors, or at least about $10^{11}$ lentiviral vectors, or at least about $10^{12}$ lentiviral vectors, or at least about $10^{13}$ lentiviral vectors, or at least about $10^{14}$ lentiviral vectors, or about $10^{10}$-$10^{14}$ lentiviral vectors, or about $10^{10}$-$10^{13}$ lentiviral vectors, or about $10^{10}$-$10^{12}$ lentiviral vectors, or about $10^{10}$, about $10^{11}$, about $10^{12}$, or about $10^{13}$ lentiviral vectors.

In embodiments, the steps of the method are performed in a closed and automated process, and suitably include monitoring with one or more of a temperature sensor, a pH sensor, a glucose sensor, a lactose sensor, an oxygen sensor, a carbon dioxide sensor, and an optical density sensor, and automatically adjusting one or more of a temperature, a pH level, a glucose level, a lactose level, an oxygen level, a carbon dioxide level, and an optical density.

Also provided herein are methods of treating a mammalian subject, suitably a human subject, with an AAV or lentiviral vector produced according to the various methods described herein. Suitably, the methods are used to treat a human subject with a gene of interest, including a gene of therapeutic interest. Administration to a human subject can include, for example, inhalation, injection, or intravenous administration, as well as other administration methods known in the art.

Additional Exemplary Embodiments

Embodiments 1 is a method for automated production of an adeno-associated virus (AAV) viral vector, comprising: introducing an engineered mammalian AAV viral producer cell into a fully enclosed cell engineering system, the engineering mammalian AAV viral producer cell including integrated into its genome: an adenovirus helper gene comprising E2A and E4Orf6 genes under control of a first derepressible promoter; an AAV gene comprising Rep and Cap genes under control of a second derepressible promoter; a viral-associated, non-coding RNA under control of a third derepressible promoter; and a repressor element of the first, second and third derepressible promoters; transducing the mammalian AAV viral producer cell with a vector encoding a gene of interest to produce a transduced viral producer cell; treating the mammalian AAV viral producer cell with a binding partner of the repressor element; activating the first, second and third derepressible promoters; expanding the transduced viral producer cell and producing the AAV viral vector within the transduced viral producer cell; and isolating the viral vector, wherein the steps are performed in a closed and automated process.

Embodiment 2 includes the method of embodiment 1, wherein the engineered mammalian AAV viral producer cell is a mammalian cell culture.

Embodiment 3 includes the method of embodiment 2, wherein the mammalian cell culture is a suspension culture.

Embodiment 4 includes the method of any of embodiments 1-3, wherein the engineered mammalian AAV viral producer cell is a Chinese hamster ovary (CHO) cell.

Embodiment 5 includes the method of any of embodiments 1-3, wherein the engineered mammalian AAV viral producer cell is a human cell.

Embodiment 6 includes the method of embodiment 5, wherein the human cell is a human embryonic kidney (HEK) cell.

Embodiment 7 includes the method of any of embodiments 1-6, wherein each of the derepressible promoters comprise a functional promoter and two tetracycline operator sequences (TetO2), and wherein the repressor element is a tetracycline repressor protein.

Embodiment 8 includes the method of embodiment 7 wherein the treating comprises treating with doxycycline.

Embodiment 9 includes the method of any of embodiments 1-8, wherein the gene of interest is a gene of therapeutic interest.

Embodiment 10 includes the method of any of embodiments 1-9, wherein an amount of AAV viral vectors produced is at least about $10^{10}$ viral vectors.

Embodiment 11 includes the method of any of embodiments 1-10, wherein the closed and automated process comprises: monitoring with one or more of a temperature sensor, a pH sensor, a glucose sensor, a lactose sensor, an oxygen sensor, a carbon dioxide sensor, and an optical density sensor, and automatically adjusting one or more of a temperature, a pH level, a glucose level, a lactose level, an oxygen level, a carbon dioxide level, and an optical density.

Embodiment 12 includes the method of any of embodiments 1-11, wherein the transducing comprises viral infection, electroporation, liposome transfection, or membrane disruption.

Embodiment 13 is a method for automated production of an adeno-associated virus (AAV) viral vector, comprising: transducing a mammalian cell stably expressing one or more nucleic acids encoding TetR and/or TetR-KRAB with: a first nucleic acid encoding an adenovirus helper gene comprising an E2A gene, a E4Orf gene and a viral-associated non-coding RNA, under control of a first derepressible promoter; a second nucleic acid encoding an AAV gene comprising Rep and Cap genes under control of a second derepressible promoter; and optionally, a third nucleic acid encoding a gene of interest under control of a third derepressible promoter; treating the mammalian cell with a binding partner of the TetR; activating the first, second and third derepressible promoters; expanding the transduced cell and producing the AAV viral vector within the transduced cell; and isolating the viral vector, wherein the steps are performed in a closed and automated process.

Embodiment 14 includes the method embodiment 13, wherein the mammalian cell is a mammalian cell culture.

Embodiment 15 includes the method of embodiment 14, wherein the mammalian cell culture is a suspension culture.

Embodiment 16 includes the method of any of embodiments 12-15, wherein the mammalian cell is a Chinese hamster ovary (CHO) cell.

Embodiment 17 includes the method of any of embodiments 12-15, wherein the mammalian cell is a human cell.

Embodiment 18 includes the method of embodiment 17, wherein the human cell is a human embryonic kidney (HEK) cell.

Embodiment 19 includes the method of any of embodiments 12-18 wherein the treating comprises treating with doxycycline.

Embodiment 20 includes the method of any of embodiments 12-19, wherein the gene of interest is a gene of therapeutic interest.

Embodiment 21 includes the method of any of embodiments 12-20, wherein an amount of AAV viral vectors produced is at least about $10^{10}$ viral vectors.

Embodiment 22 includes the method of any of embodiments 12-21, wherein the closed and automated process comprises: monitoring with one or more of a temperature sensor, a pH sensor, a glucose sensor, a lactose sensor, an oxygen sensor, a carbon dioxide sensor, and an optical density sensor, and automatically adjusting one or more of a temperature, a pH level, a glucose level, a lactose level, an oxygen level, a carbon dioxide level, and an optical density.

Embodiment 23 includes the method of any of embodiments 12-22, wherein the transducing comprises viral infection, electroporation, liposome transfection, or membrane disruption.

Embodiment 24 is a method for automated production of a lentiviral vector, comprising: introducing an engineered mammalian lentiviral vector producer cell into a fully enclosed cell engineering system, the engineering mammalian lentiviral vector producer cell including integrated into its genome: a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the nucleic acid sequence is flanked on both the 5' and 3' ends by sequences resulting from the recombination of transposon-specific inverted terminal repeats (ITRs); transducing the mammalian lentiviral vector producer cell with a vector encoding a gene of interest to produce a transduced viral producer cell; activating the first, second and third promoters; expanding the transduced viral producer cell and producing the lentiviral vector within the transduced viral producer cell; and isolating the viral vector, wherein the steps are performed in a closed and automated process.

Embodiment 25 includes the method of embodiment 24, wherein the engineered mammalian lentiviral vector producer cell is a mammalian cell culture.

Embodiment 26 includes the method of embodiment 25, wherein the mammalian cell culture is a suspension culture.

Embodiment 27 includes the method of any of embodiments 24-26, wherein the engineered mammalian lentiviral vector producer cell is a human cell.

Embodiment 28 includes the method of embodiment 27, wherein the human cell is a human embryonic kidney (HEK) cell.

Embodiment 29 includes the method of any of embodiments 24-28, wherein the GAG gene is an HIV GAG gene and the POL gene is an HIV POL gene.

Embodiment 30 includes the method of any of embodiments 24-29, wherein the lentiviral envelope gene is a Vesicular Somatitis Virus Glycoprotein (VSV-G) gene.

Embodiment 31 includes the method of any of embodiments 24-30, wherein the first, second and third promoters are derepressible promoters.

Embodiment 32 includes the method of embodiment 31, wherein the engineered mammalian lentiviral vector producer cell further includes integrated into its genome a repressor element of the first, second and third derepressible promoters Embodiment 33 includes the method of embodiment 32, wherein each of the derepressible promoters comprises a functional promoter and a tetracycline operator sequence (TetO), and the repressor element is a tetracycline repressor protein.

Embodiment 34 includes the method of embodiment 33, further comprising a Kruppel-associated box sequence following a sequence encoding the tetracycline repressor protein.

Embodiment 35 includes the method of any of embodiments 24-34, wherein the transposon-specific ITRs are Lepidopteran transposon (PIGGYBAC®) ITRs.

Embodiment 36 includes the method of any of embodiments 24-35, wherein the gene of interest is a gene of therapeutic interest.

Embodiment 37 includes the method of any of embodiments 24-36, wherein an amount of lentiviral vectors produced is at least about $10^{10}$ viral vectors.

Embodiment 38 includes the method of any of embodiments 24-37, wherein the closed and automated process comprises: monitoring with one or more of a temperature sensor, a pH sensor, a glucose sensor, a lactose sensor, an oxygen sensor, a carbon dioxide sensor, and an optical density sensor, and automatically adjusting one or more of a temperature, a pH level, a glucose level, a lactose level, an oxygen level, a carbon dioxide level, and an optical density.

Embodiment 39 includes the method of any of embodiments 24-38, wherein the transducing comprises viral infection, electroporation, liposome transfection, or membrane disruption.

Embodiment 40 is a method for automated production of a lentiviral vector, comprising: introducing a mammalian cell into a fully enclosed cell engineering system; transducing a mammalian cell with: a first nucleic acid encoding a lentiviral regulator of expression of virion proteins (REV) gene under control of a first promoter and an envelope glycoprotein gene under control of a second promoter; a second nucleic acid encoding a gene of interest under control of a third promoter; and a third nucleic acid encoding a lentiviral group specific antigen (GAG) gene and a lentiviral polymerase (POL) gene both under control of a fourth promoter, expanding the transduced cell and producing the lentiviral vector within the transduced cell; and isolating the viral vector, wherein the steps are performed in a closed and automated process.

Embodiment 41 includes the method of embodiment 40, wherein the mammalian cell is a mammalian cell culture.

Embodiment 42 includes the method of embodiment 41, wherein the mammalian cell culture is a suspension culture.

Embodiment 43 includes the method of any of embodiments 40-42, wherein the mammalian cell is a human cell.

Embodiment 44 includes the method of embodiment 43, wherein the human cell is a human embryonic kidney (HEK) cell.

Embodiment 45 includes the method of any of embodiments 40-44, wherein the GAG gene is an HIV GAG gene and the POL gene is an HIV POL gene.

Embodiment 46 includes the method of any of embodiments 40-46, wherein the envelope glycoprotein gene is a Vesicular Somatitis Virus Glycoprotein (VSV-G) gene, and wherein the VSV-G gene and the REV gene are codon optimized.

Embodiment 47 includes the method of any of embodiments 40-46, wherein the gene of interest is a gene of therapeutic interest.

Embodiment 48 includes the method of any of embodiments 40-47, wherein an amount of lentiviral vectors produced is at least about $10^{10}$ viral vectors.

Embodiment 49 includes the method of any of embodiments 40-48, wherein the closed and automated process comprises: monitoring with one or more of a temperature sensor, a pH sensor, a glucose sensor, a lactose sensor, an oxygen sensor, a carbon dioxide sensor, and an optical density sensor, and automatically adjusting one or more of a temperature, a pH level, a glucose level, a lactose level, an oxygen level, a carbon dioxide level, and an optical density.

Embodiment 50 includes the method of any of embodiments 40-49, wherein the transducing comprises viral infection, electroporation, liposome transfection, or membrane disruption.

Embodiments 51 is a AAV viral vector produced by the methods of any of embodiments 1-23.

Embodiment 52 is lentivirus vector produced by the methods of any of embodiments 14-50.

Embodiment 53 is a method of treatment with an AAV vector, comprising: administering the AAV vector of embodiment 51 to a mammalian subject.

Embodiment 54 includes the method of embodiment 53, wherein the administering comprises inhalation, injection or intravenous administration.

Embodiment 55 is a method of treatment with a lentiviral vector, comprising: administering the lentiviral vector of claim 52 to a mammalian subject.

Embodiment 56 includes the method of embodiment 55, wherein the administering comprises inhalation, injection or intravenous administration.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All publications, patents and patent applications mentioned in this specification are herein incorporated by reference to the same extent as if each individual publication, patent or patent application was specifically and individually indicated to be incorporated by reference.

What is claimed is:

1. A method for automated production of an adeno-associated virus (AAV) viral vector, comprising:
   (a) introducing an engineered mammalian AAV viral producer cell into a fully enclosed cell engineering system, the engineered mammalian AAV viral producer cell including integrated into its genome:
      i. an adenovirus helper gene comprising E2A and E4Orf6 genes under control of a first derepressible promoter;
      ii. an AAV gene comprising Rep and Cap genes under control of a second derepressible promoter;
      iii. a viral-associated, non-coding RNA under control of a third derepressible promoter; and
      iv. a repressor element of the first, second and third derepressible promoters;
   (b) transducing the mammalian AAV viral producer cell with an AAV viral vector encoding a gene of interest to produce a transduced viral producer cell;
   (c) treating the mammalian AAV viral producer cell with a binding partner of the repressor element;
   (d) activating the first, second and third derepressible promoters;
   (e) expanding the transduced viral producer cell and producing the AAV viral vector within the transduced viral producer cell; and
   (f) isolating the AAV viral vector,
   wherein (a) through (f) are performed in a closed and automated process, and
   wherein the closed and automated process further comprises:
   (g) monitoring with one or more of a temperature sensor, a pH sensor, a glucose sensor, a lactose sensor, an oxygen sensor, a carbon dioxide sensor, and an optical density sensor, and
   (h) automatically adjusting media circulation based on the monitoring.

2. The method of claim 1, wherein the engineered mammalian AAV viral producer cell is a mammalian cell culture.

3. The method of claim 2, wherein the mammalian cell culture is a suspension culture.

4. The method of claim 2, wherein the mammalian cell culture is an adherent culture.

5. The method of claim 2, wherein the transducing comprises viral infection, electroporation, liposome transfection, or membrane disruption.

6. The method of claim 1, wherein each of the derepressible promoters comprise a functional promoter and two tetracycline operator sequences (TetO$_2$), wherein the repressor element is a tetracycline repressor protein.

7. A method for automated production of an adeno-associated virus (AAV) viral vector, comprising:
(a) transducing a mammalian cell stably expressing one or more nucleic acids encoding TetR and/or TetR-KRAB with:
  i. a first nucleic acid encoding an adenovirus helper gene comprising an E2A gene, an E4Orf gene and a viral-associated non-coding RNA, under control of a first derepressible promoter;
  ii. a second nucleic acid encoding an AAV gene comprising Rep and Cap genes under control of a second derepressible promoter; and
  iii. optionally, a third nucleic acid encoding a gene of interest under control of a third derepressible promoter;
(b) treating the mammalian cell with a binding partner of the TetR;
(c) activating the first, second and third derepressible promoters;
(d) expanding the transduced cell and producing the AAV viral vector within the transduced cell; and
(e) isolating the AAV viral vector,
wherein (a) through (e) are performed in a closed and automated process, and
wherein the gene of interest is a gene of therapeutic interest.

8. The method of claim 7, wherein an amount of AAV viral vectors produced is at least about $10^{10}$ viral vectors.

9. The method of claim 7, further comprising monitoring with one or more of a temperature sensor, a pH sensor, a glucose sensor, a lactose sensor, an oxygen sensor, a carbon dioxide sensor, and an optical density sensor.

10. The method of claim 9, further comprising automatically adjusting media circulation based on the monitoring.

11. The method of claim 9, wherein each of the derepressible promoters comprise a functional promoter and two tetracycline operator sequences (TetO$_2$).

12. A method for automated production of a lentiviral vector, comprising:
(a) introducing a mammalian cell into a fully enclosed cell engineering system;
(b) transducing the mammalian cell with:
  i. a first nucleic acid encoding a lentiviral regulator of expression of virion proteins (REV) gene under control of a first promoter and an envelope glycoprotein gene under control of a second promoter;
  ii. a second nucleic acid encoding a gene of interest under control of a third promoter; and
  iii. a third nucleic acid encoding a lentiviral group specific antigen (GAG) gene and a lentiviral polymerase (POL) gene both under control of a fourth promoter,
(c) expanding the transduced cell and producing the lentiviral vector within the transduced cell; and
(d) isolating the lentiviral vector,
wherein (a) through (d) are performed in a closed and automated process, and
wherein the closed and automated process further comprises:
  (a) monitoring with one or more of a temperature sensor, a pH sensor, a glucose sensor, a lactose sensor, an oxygen sensor, a carbon dioxide sensor, and an optical density sensor, and
  (b) automatically adjusting media circulation based on the monitoring.

13. The method of claim 12, wherein the transducing comprises viral infection, electroporation, liposome transfection, or membrane disruption.

14. The method of claim 12, wherein the gene of interest is a gene of therapeutic interest.

15. The method of claim 12, wherein an amount of lentiviral vectors produced is at least about $10^{10}$ viral vectors.

16. The method of claim 12, further comprising monitoring with one or more of a temperature sensor, a pH sensor, a glucose sensor, a lactose sensor, an oxygen sensor, a carbon dioxide sensor, and an optical density sensor.

17. The method of claim 12, wherein each of the promoters comprise a functional promoter and two tetracycline operator sequences (TetO$_2$).

* * * * *